United States Patent [19]
Khokhar et al.

[11] Patent Number: 5,393,909
[45] Date of Patent: Feb. 28, 1995

[54] DIAMINE PLATINUM COMPLEXES AS ANTITUMOR AGENTS

[75] Inventors: Abdi R. Khokhar; Zahid H. Siddik, both of Houston, Tex.

[73] Assignee: Board of Regents, The University of Texas System, Austin, Tex.

[21] Appl. No.: 200,395

[22] Filed: Feb. 23, 1994

Related U.S. Application Data

[60] Continuation-in-part of Ser. No. 978,788, Nov. 19, 1992, Pat. No. 5,288,887, which is a continuation-in-part of Ser. No. 927,201, Aug. 7, 1992, Pat. No. 5,318,962, which is a continuation-in-part of Ser. No. 624,795, Dec. 7, 1990, abandoned, which is a division of Ser. No. 274,824, Nov. 22, 1988, Pat. No. 5,041,578.

[51] Int. Cl.$^6$ ........................ C07F 15/00; A61K 31/28
[52] U.S. Cl. ................................................. 556/137
[58] Field of Search .................. 556/136, 137; 514/492, 514/184

[56] References Cited

U.S. PATENT DOCUMENTS

| | | | |
|---|---|---|---|
| 3,904,663 | 9/1975 | Tobe et al. | 556/137 |
| 4,115,418 | 9/1978 | Gale et al. | 556/137 |
| 4,137,248 | 1/1979 | Gale et al. | 556/137 |
| 4,140,707 | 2/1979 | Cleare et al. | 556/137 |
| 4,169,846 | 10/1979 | Kidani et al. | 556/137 |
| 4,203,912 | 5/1980 | Hydes et al. | 556/26 |
| 4,225,529 | 9/1980 | Hydes et al. | 556/137 |
| 4,230,631 | 10/1980 | Hydes et al. | 556/26 |
| 4,256,652 | 3/1981 | Kidani et al. | 556/137 |
| 4,271,085 | 6/1981 | Amundsen | 556/137 |
| 4,431,666 | 2/1984 | Bulten et al. | 514/492 |
| 4,466,924 | 8/1984 | Verbeek et al. | 556/137 |
| 4,560,781 | 12/1985 | Totani et al. | 556/137 |
| 4,562,275 | 12/1985 | Speer et al. | 556/7 |
| 4,565,884 | 1/1986 | Andrulis, Jr. et al. | 556/137 |
| 4,575,550 | 3/1986 | Totani | 536/121 |
| 4,577,038 | 3/1986 | Totani et al. | 556/137 |
| 4,578,491 | 3/1986 | Amundsen et al. | 556/137 |
| 4,584,316 | 4/1986 | Rosenberg et al. | 514/492 |
| 4,584,392 | 4/1986 | Smith et al. | 556/137 |
| 4,594,418 | 6/1986 | Speer et al. | 544/225 |
| 4,599,352 | 7/1986 | Narayanan et al. | 514/492 |

(List continued on next page.)

FOREIGN PATENT DOCUMENTS

| | | |
|---|---|---|
| 569425 | 1/1988 | Australia . |
| 898614 | 5/1984 | Belgium . |
| 30039272 | 11/1981 | European Pat. Off. . |
| 30098121 | 1/1984 | European Pat. Off. . |
| 0113504 | 7/1984 | European Pat. Off. . |
| 0130482 | 1/1985 | European Pat. Off. . |
| 0136012 | 4/1985 | European Pat. Off. . |
| 0147926 | 7/1985 | European Pat. Off. . |
| 31055705 | 9/1985 | European Pat. Off. . |
| 10185225 | 6/1986 | European Pat. Off. . |
| 0193936 | 9/1986 | European Pat. Off. . |
| 0237450 | 9/1987 | European Pat. Off. . |
| 2160867A | 1/1986 | United Kingdom . |
| WO87/02364 | 4/1987 | WIPO . |
| WO88/03925 | 6/1988 | WIPO . |

OTHER PUBLICATIONS

Perez-Soler et al., "Treatment and Prophylaxis of Experimental Liver Metastases of M5076 Reticulosarcoma with cis-Bis-neodecanoato-trans-R,R-1,2-diaminocyclohexaneplatinum (II) Encapsulated in Multilamellar Vesicles", Cancer Research, 47:6462-6466 (Dec. 1987).

(List continued on next page.)

*Primary Examiner*—Arthur C. Prescott
*Attorney, Agent, or Firm*—Arnold, White & Durkee

[57] ABSTRACT

Novel 1,4-diaminocyclohexane platinum II and platinum IV complexes were synthesized which show activity in vivo against tumor models resistant to cis-platin and tetraplatin. The novel complexes include the sulfato, chloro, hydroxyl, acetato methylmalonato, tartronato and 1,1-cyclobutane dicarboxylato as leaving ligands and 1,4-DACH amine as non-leaving ligands. The complexes showed good in vitro cytotoxic activity against murine leukemia L1210/0 and human ovarian A2780 cell lines. High in vivo activity was shown against L1210 leukemia cells and against cis-platin resistant L1210/DDP and tetraplatin resistant L1210/DACH. Excellent antitumor activity against M5076 was also exhibited by the new complexes. Additionally, the platinum complexes did not elicit any indication of nephrotoxicity in the in vivo tests.

11 Claims, 2 Drawing Sheets

U.S. PATENT DOCUMENTS

| | | | |
|---|---|---|---|
| 4,614,811 | 9/1986 | Gandolfi | 556/137 |
| 4,617,189 | 10/1986 | Stockel et al. | 424/702 |
| 4,657,927 | 4/1987 | Cleare et al. | 514/492 |
| 4,658,047 | 4/1987 | Vishnurajjala | 556/137 |
| 4,658,048 | 4/1987 | Totani et al. | 556/137 |
| 4,659,849 | 4/1987 | Drobnik et al. | 556/137 |
| 4,661,516 | 4/1987 | Brown et al. | 514/492 |
| 4,665,210 | 5/1987 | Bitha et al. | 556/137 |
| 4,670,458 | 6/1987 | Hlavka et al. | 514/492 |
| 4,673,754 | 6/1987 | Smith et al. | 556/137 |
| 4,675,336 | 6/1987 | Bitha et al. | 514/492 |
| 4,680,308 | 7/1987 | Schwartz et al. | 514/492 |
| 4,707,352 | 11/1987 | Stavrianpoulos | 424/1.17 |
| 4,720,504 | 1/1988 | Andrulis, Jr. et al. | 514/492 |
| 4,739,087 | 4/1988 | Speer et al. | 556/137 |
| 4,758,588 | 7/1988 | Brown et al. | 514/492 |
| 4,760,155 | 7/1988 | Heffernan et al. | 556/136 |
| 4,760,156 | 7/1988 | Heffernan | 556/136 |
| 4,760,157 | 7/1988 | Child et al. | 556/137 |
| 4,845,124 | 7/1989 | Kidani et al. | 514/492 |
| 4,861,905 | 8/1989 | Nowatari et al. | 556/40 |
| 4,968,826 | 11/1990 | Totani et al. | 556/137 |
| 5,011,959 | 4/1991 | Khokhar et al. | 556/137 |
| 5,041,578 | 8/1991 | Khokhar | 556/137 |
| 5,244,919 | 9/1993 | Abrams et al. | 514/492 |
| 5,288,887 | 2/1994 | Khokhar et al. | 556/137 |

OTHER PUBLICATIONS

Maeda et al., "Liposoluble Platinum (II) Complexes with Antitumor Activity", *Japan Journal Cancer Research*, 77:523–525 (Jun. 1986).

Vollano et al., "Comparative Antitumor Studies on Platinum (II) and Platinum (IV) Complexes Containing 1,2-Diaminocyclohexane", *J. Med. Chem.*, 30:716–719 (1987).

Belg. BE 898,614, "Cis-1,2-Diaminocyclohexane Platinum Complexes", *Chem. Abstracts* 101:177510w (1984).

Kihari, "Organoplatinum Complexes as Antineoplastics", *Chemical Abstracts* 105:134160X (1984).

Craciunescu, "On the Preparation, Antitumor and Cytotoxic Evaluation of Some New Analogues of the Cis-Dichloro (1,2-Diamino-Cyclohexane) Platinum (II) Complex", *Eur. J. Med. Chem.*, 353–357 (1984).

Sur, "Effect of Liposomal Encapsulation of Cis-- Platinum Diamminodichloride in the Treatment of Ehrlich Ascites Carcinoma:", *Oncology*, 40:372–376 (1983).

Freise, "Pharmacokinetics of Liposome Encapsulated Cisplatin in Rats", *Archives etc.*, 258:180–192 (1982).

Kaledin, "Intralymphatic Administration of Liposome-Encapsulated Drugs to Mice: Possibility for Suppression of the Growth of Tumor Metastases in the Lymph Nodes", *JNCL*, 66:881–886 (1981).

Deliconstantinos, "Incorporation of Cis-Dichlorobis-cyclopentylamineplatinum (II) into Liposome Enhances its Uptake by ADJ/PC6A Tumors Implanted Subcutaneously into Mice", *Biochem. Soc. Trans.*, 5:1326–1328 (1977).

Yatvin, "Selective Delivery by Hyperthermia of Liposome Encapsulated Cis Dichlorodiamine Platinum (II) and Tumor Growth Delay", (Meeting Abstract), *Proc. Am. Assoc. Cancer. Res.*, 21:281 (1980).

Schwartz, "Preparation and Antitumor Evaluation of Water-Soluble Derivatives of Dichloro (1,2-diaminocyclohexane) platinum (II)", *Chemical Abstracts*, 88:16014K (1978).

Perez-Soler, "Toxicity and Antitumor Activity of cis-Bis-cyclopentenecarboxylato-1,2-diaminocyclohexane Platinum (II) Encapsulated in Multilamellar Vescicles", *Cancer Research* 46, 6269–6273 (1986).

Connors, "New Platinum Complexes with Anti-Tumor Activity", *Chem. Biol. Interactions*, 5:415–424 (1972).

Ridgway, "Analogs of Sulfato 1,2-Diaminocyclohexane Platinum (II). I. Modifications in Leaving Ligand", *J. Clin. Hematol. Oncol.* 7:220–229 (1977).

Burchenal, "Rationale of Combination Chemotherapy", *Chemical Abstracts* 93:125661t (1980).

Appleton, "Reactions of Platinum (II) Aqua Complexes", *Chemical Abstracts* 101:182656c (1984).

Speer, "Malonato-1,2-diaminocyclohexaneplatinum (II), a Potential Antitumor Agent", *Chemical Abstracts* 84:54030n (1976).

Khokhar, "The Synthesis and Antitumor Properties of a Series of Water Soluble Carboxylato (1,2-diaminocyclohexane) platinum (II) Complexes", *Chemical Abstracts* 103:22630p (1980).

Tzu, "Synthesis and Study of Some Platinum Complexes with Dicarboxylic Acids", *Chemical Abstracts* 94:218774t (1981).

Eastman et al., "Mechanisms of Resistance to Platinum Drugs", *Platinum and Other Metal Coordination Compounds in Cancer Chemotherapy*, Fifth International Symposium, Abano, Padua, Italy, 1987.

DIAMINE PLATINUM COMPLEXES AS ANTITUMOR AGENTS

The United States own rights in the present invention pursuant to grant No. CA 41581 from the National Institutes of Health.

This patent application is a continuation-in-part of U.S. Ser. No. 07/978,788, filed Nov. 19, 1992; now issued as U.S. Pat. No. 5,288,887 the entire text of which is herein incorporated by reference and without disclaimer and which is a continuation-in-part of U.S. Ser. No. 07/927,201, filed on Aug. 7, 1992, now U.S. Pat. No. 5,318,962, which was a continuation-in-part of U.S. Ser. No. 07/624,795, filed on Dec. 7, 1990, now abandoned, which was a divisional of U.S. Ser. No. 07/274,824, filed on Nov. 22, 1988, now issued as U.S. Pat. No. 5,041,578, all of which the entire text is incorporated by reference and without disclaimer.

BACKGROUND OF THE INVENTION

1. Field of the Invention

The present invention relates generally to 1,4-diaminocyclohexane (DACH) platinum (II) and (IV) complexes and to compositions and methods of use of these compounds in treating neoplastic conditions.

2. Description of Related Art

One of the major limitations to clinical use of cancer therapeutic agents is the development of resistance to such agents. Currently it is believed that resistance is one of the major limitations in effecting a cure. The problem of drug resistance has been observed with numerous drugs, including the platinum coordination complexes used to treat certain types of solid tumors and leukemias.

Clinical resistance is frequently encountered as recurrence of the tumor subsequent to drug therapy. Resistance is prevalent in most courses of treatment and, therefore, most therapeutic regimes now include several different drugs as a method of circumventing resistance. Mechanisms of resistance to platinum drugs have been investigated (Eastman, et al., 1987) and certain patterns of resistance to platinum coordination complexes reported. The mechanisms of resistance, however, are not completely understood. While believed to occur at the cellular level, resistance may also involve alterations in pharmacodynamics. An examination of patterns of cross-resistance of cis-DDP (Eastman, et al., 1987) indicates that there is a pattern of cross-resistant with other cis-platin complexes.

Despite development of resistance, cis-platin is a clinically important anti-neoplastic agent with particular utility in the treatment of testicular and ovarian cancer. In certain instances, patients with ovarian may not be cured with standard dose cis-platin regiments. The appropriate dose level of cis-platinum appears to be a critical factor in achieving optimum results. However, there are several problems associated with the use of high doses of cis-platinum including toxicity, particularly nephrotoxicity.

Certain platinum-based drugs are known to have useful antitumor activity. For example, cis-diaminedichloroplatinum(II) (CDDP), more commonly known as cis-platin, represents the first effective metal antitumor drug to be used routinely in the clinic, either alone or in combination with other drugs to treat certain solid tumors such as ovarian tumors. Unfortunately, cis-platin treatment is associated with numerous undesirable side effects, including nephrotoxicity and a relatively narrow spectrum of activity against neoplasms.

At both clinical and preclinical levels, two major impediments to the use of CDDP have been recognized: first, the frequent cumulative and irreversible toxicity and secondly, the development of drug resistance, a major limitation to clinical use of many therapeutic agents used in cancer treatment and a particular problem in the use of platinum drugs. The precise mechanism of drug resistance is not known, although observed patterns of resistance to platinum coordination complexes have been studied and such patterns indicate potential mechanisms of resistance (Eastman, et al., 1987).

Several derivatives of cis-platinum have been synthesized in an attempt to overcome these disadvantages and some progress has been made in identifying certain platinum compounds with high aqueous solubility, lowered nephrotoxicity and high antitumor activity. Platinum (IV) complexes as anti-tumor agents have been examined by Abrams, et al. (1993); and a wide range of 1,2-diaminocyclohexane platinum (IV) (Khokhar, 1991) and platinum (II) complexes (Khokhar, et al., 1991) have been synthesized and evaluated.

Despite the high number of platinum compounds available for clinical use, the development of resistance remains a major problem. There is therefore a need to develop platinum drugs which have improved antitumor activity and toward which tumors do not readily display cross resistance.

SUMMARY OF THE INVENTION

The present invention seeks to overcome these and other disadvantages of current anti-tumor therapies employing cis-platin compounds by providing novel diamineplatinum complexes which show outstanding potency in vitro and curative antitumor activity in vivo against cis-platin and tetraplatin-resistant tumors.

Unexpectedly, several 1,4-DACH complexes show antitumor activity against cis-platin and tetraplatin-resistant leukemia and solid tumors in animal models. Additionally, some of the effective compounds are distinctly more cytotoxic than tetraplatin and cis-platin as demonstrated in vitro. As shown in in vivo studies, the new compounds lack the nephrotoxicity of cis-platin and tetraplatin, yet show good activity in standard assay systems.

The present invention also concerns antitumor compositions which include an effective amount of one or more of the new platinum compounds included with a pharmaceutically acceptable carrier. Solutions of the complexes as the free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The active compounds may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents; for example, sugars or salts such as sodium chloride. Prolonged absorption of the injectable compositions can be brought about by the use in the compositions of agents which delay absorption, such as aluminum monostearate or gelatin, for example.

Sterile injectable solutions are prepared by incorporating the platinum complexes in the required amount in the appropriate solvent with various of the other ingredients enumerated above, as required, followed by filter sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum drying and freeze drying techniques which yield a powder of the active ingredient plus any additional desired ingredients from a previously sterile filtered solution thereof.

Parenteral administration, for example, may be in a suitable buffered aqueous solution and the liquid diluent first rendered isotonic with sufficient saline or glucose. These particular aqueous solutions are especially appropriate for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see, for example, "Remington's Pharmaceutical Sciences", 15th Edition, pages 1035–1038 and 1570–1580). Some variation in dosage will be necessary depending on the condition of the subject being treated. The person responsible for administration will, in any event, determine the appropriate dose for the individual subject.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

Upon formulation, solutions containing the active platinum complex will be administered in a manner compatible with the dosage formulation and in such amount as is therapeutically effective. The formulations are easily administered in a variety of dosage forms such as injectable solutions, drug release capsules, implants or in combination with carriers such as liposomes or microcapsules.

The compounds, compositions and methods of the present invention possess significant advantages over the prior art, including lack of nephrotoxicity and particularly in having an effect on cis-platin and tetraplatin resistant leukemias and solid tumors.

DETAILED DESCRIPTION OF PREFERRED EMBODIMENTS

The present invention concerns novel platinum complexes synthesized with selected ligands in order to improve certain pharmacological characteristics, such as increased efficacy, decreased host toxicity, increased water solubility and lack of cross resistance with cis-platin and tetraplatin. The general chemical structure of the new platinum complexes is shown below.

where Y is sulfato, carboxylato, oxalato, cyclobutanedicarboxylato, methylmalonato, tartronato, malonato, or chloride ligands and $X_1$ and $X_2$ are chloride, hydroxide or acetate.

The compounds of the present invention are prepared by well-known chemical procedures analogous to those described in U.S. Pat. Nos. 5,011,959 and 5,041,578. Surprisingly, these compounds were not cross resistant with cis-platin or tetraplatin, indicating use in therapies where the use of platinum antitumor drugs is indicated.

Several 1,4-diaminocyclohexane (DACH) platinum II and IV complexes were synthesized as set forth in the procedures of Example 1. Structures were confirmed by chemical and spectral analysis.

Antitumor activities of selected compounds were determined against L1210/0 and A2780 tumor lines. In these tumor models, tetraplatin was approximately 2–3 fold more potent than cis-platin, and both compounds were more effective against murine than human cells. The cis-1,4-DACH-platinum complexes on the other hand were generally more potent (up to 4-fold) against human A2780 cells, although in some cases were somewhat more cytotoxic.

EXAMPLE 1

Preparation of 1,4-DACH Platinum Complexes

Cis- 1,4-diaminocyclohexane- 1,1-cyclobutanedicarboxylato-platinum(II).H2O [1]: Potassium tetrachloroplatinate(II) (6.25 g; 15 mM) was dissolved in 100 ml of water. Dimethylsulfoxide (2.34 g; 30 mM) in 10 ml of water was added to it. The reaction mixture was kept at room temperature for two days. The pale yellow needles of Cis-dichloro-bis-dimethylsulfoxideplatinum(II), were obtained, filtered, washed with cold water and dried in vacuo. Yield: 74%. Cis-dichloro-bis-dimethylsulfoxideplatinum(II) (6.16 g; 14.6 mM) was dissolved in 250 ml of warm water. To this solution was added a suspension of silver salt of 1,1-cyclobutanedicarboxylic acid (5.07 g; 14.16 mM). The reaction mixture was kept stirring for 24 h protecting from light at room temperature. The solution was filtered and the yellow filtrate was evaporated to 50 ml under reduced pressure at 35° C. and was kept in ice. The white crystalline 1,1-cyclobutanedicarboxylato-bis-dimethylsulfoxide-platinum(II) was isolated, washed with cold water and dried under vacuum. Yield: 70%. To a hot solution of 1,1-cyclobutanedicarboxylato-bis-dimethylsulfoxide-platinum(II) (4.94 g; 10 mM) in 300 ml of water was added a solution of Cis-1,4-diaminocyclohexane (1.14 g; 10 mM) in 10 ml of water. The reaction mixture was kept stirring at 90° C. for 1½ h. The completion of reaction was checked by HPLC. The solution was filtered while hot, cooled and evaporated to a minimum volume under reduced pressure at 35° C. and kept in ice. The off white compound was precipitated, filtered and recrystallized from water. A white crystalline product, 1 was obtained and dried in vacuo. Yield: 50%.

Cis- 1,4-Diaminocyclohexaneaquasulfatoplatinum(II) [2]: Cis- 1,4-diaminocyclohexane-1,1-cyclobutanedicarboxylatoplatinum(II) (2.00 g; 4.26 mM) was dissolved in 30 ml of conc. HCl and kept stirring for 6 days at room temperature. The yellow solution was obtained, which was evaporated slowly at room temperature. After 2–3 days, the yellow crystalline product, Cis- 1,4-diaminocyclo-hexanedichloroplatinum(II) was separated, filtered and washed with water and dried under vacuum. Yield: 80%. To a suspension of Cis-1,4-diaminocyclohexanedichloroplatinum(II) (0.92 g; 2.41 mM) in 50 ml of water, an aqueous solution of silver sulfate (0.72 g; 2.32 mM) was added. The reaction mixture was kept stirring for 24 h in the dark. The pale yellow solution was filtered and the filtrate was evaporated to dryness under reduced pressure at 35° C. The yellow solid, 2 was obtained, which was dried under vacuum. Yield: 90%.

Cis- 1,4-Diaminocyclohexanemethylmalonato-platinum(II). H2O [3]: Cis-1,4-diaminocyclohexaneaquasulfatoplatinum(II) (0.85 g; 2.00 mM) was dissolved in 150 ml of water and an aqueous solution of sodium salt of methylmalonic acid (0.24 g; 2.00 mM) was added to it. The reaction mixture was stirred for 10 h. An off white precipitate was obtained, which was filtered and recrystallized from hot water. A white crystalline product 3 was obtained. Yield: 75 %.

Cis-1,4-diaminocyclohexanetartronatoplatinum(II) (4); Cis-1,4-diaminocyclohexaneoxalatoplatinum(II) (5); Cis-1,4-diaminocyclohexanemalonatoplatinum(II) (6): These complexes were prepared in a manner similar to that complex 3, by interacting Cis-1,4-diaminocyclohexaneaquasulfatoplatinum(II) with the sodium salts of corresponding dicarboxylic acids.

Cis-1,4-Diaminocyclohexanetetrachloroplatinum-(IV) [7]: Cis-1,4-diaminocyclohexane-1,1-cyclobutanedicarboxylatoplatinum(II) (1.00 g; 2.13 mM) was dissolved in 200 ml of water and excess of (15 ml) 30% H2O2 was added to it. The reaction mixture was stirred for 15 h at room temperature. A clear colorless solution was obtained which was evaporated to dryness under reduced pressure at 35° C. A white solid, Cis-1,4-diaminocyclohexane-1,1-cyclobutanedicarboxylatodihydroxoplatinum(IV) (0.84 g; 1.73 mM) was obtained, which was dissolved in 50 ml of conc. HCl and stirred for 4 days at room temperature. The solution was kept at room temperature for slow evaporation. A yellow crystalline product 7 was obtained, filtered and washed with water and dried under vacuum. Yield: 70%.

Cis-1,4-diaminocyclohexanedichlorodihydroxoplatinum(IV) [8]: To a suspension of Cis-1,4-diaminocyclohexanedichloroplatinum(II) (0.76 g; 2.00 mM) in 100 ml of water, 10 ml of 30% H2O2 was added. The reaction mixture was kept stirring for 2 days at room temperature. A clear yellow color solution was obtained. It was filtered and evaporated to dryness under reduced pressure at 35° C. The yellow solid obtained was redissolved in excess of water, evaporated to a minimum volume and kept for slow evaporation. A yellow crystalline compound 8 was separated, which was filtered, washed with cold water and dried under vacuum. Yield: 60%.

Cis-1,4-diaminocyclohexane- 1,1-cyclobutanedicarboxylato-dichloroplatinum(IV) [9]: 200 ml of 0.02N HCl 1 0.15 g; 4.00 mM) was added to Cis-1,4- diaminocyclohexane-1,1-cyclobutane-dicarboxylatodihydroxoplatinum(IV) (0.97 g; 2.00 mM) and stirred. The white solid was dissolved immediately in HCl and a clear colorless solution formed. The reaction mixture was kept stirring for 15 days at room temperature. The color of the solution changed from colorless to pale yellow. The solution was filtered and evaporated to dryness at 35° C. under reduced pressure. A pale yellow solid was obtained, which was redissolved in 100 ml of methanol. The volume of the solution was reduced to 10 ml and precipitated with acetone. The precipitate was separated by filtration and washed several times with acetone. The pale yellow solid obtained was dissolved in 50 ml of methanol, concentrated to 5 ml and kept for slow evaporation at room temperature. Slowly pale yellow needles were formed, which were filtered, washed with methanol, acetone and dried in vacuo. Yield: 50%.

Cis-1,4-diaminocyclohexaneoxalatodichloroplatinum(IV) [10]: This complex was prepared according to a method similar to that complex 9, by the reaction of 0.02N HCl with Cis-1,4-diamino-cyclohexaneoxalatodihydroxoplatinum(IV). Yield: 60%.

Cis-1,4-diaminocyclohexanedichlorodiacetatoplatinum (IV) [11]: Cis- 1,4-diaminocyclohexanedichlorodihydroxoplatinum (IV) compound no. [8](0.414 g; 1.00 mM) was suspended in 100 ml of chloroform and 1.88 ml (10 mM) of acetic anhydride (10 fold) was added. The mixture was stirred for 15 days at room temperature, and 50 ml of 90% methanol was added to the mixture to give clear yellow solution which was kept stirring for one hour. The solution was evaporated to dryness under reduced pressure at 30° C. to give a pale yellow solid. It was redissolved in 25 ml of acetone and filtered. The flitrate was evaporated to dryness to give a pale yellow substance, which was recrystallized from methanol. Yield: 50%.

Table 1 shows analytical data for the synthesized 1,4-DACH complexes. Table 2 provides spectroscopic data, supporting product structures.

TABLE 1

Analytical data for platinum complexes

| No. | Complex | Found (Calcd.), % | | |
|---|---|---|---|---|
| | | C | H | N |
| 1. | 1,4-DACH*-1,1-cyclobutane-dicarboxylatoplatinum(II) $H_2O$ | 30.98 (30.68) | 5.05 (4.73) | 5.98 (5.78) |
| 2. | 1,4-DACH-aquasulfatoplatinum(II) | 16.95 (17.02) | 3.40 (3.30) | 6.32 (6.61) |
| 3. | 1,4-DACH-methylmalonatoplatinum(II).$H_2O$ | 27.18 (27.10) | 4.55 (4.55) | 6.32 (6.32) |
| 4. | 1,4-DACH-tartronatoplatinum(II) | 25.21 (25.30) | 3.76 (3.77) | 6.47 (6.55) |
| 5. | 1,4-DACH-oxalatoplatinum-(II) | 24.37 (24.18) | 3.68 (3.55) | 7.26 (7.05) |
| 6. | 1,4-DACH-malonatoplatinum-(II) | 26.17 (26.28) | 3.74 (3.92) | 6.61 (6.81) |
| 7. | 1,4-DACH-tetrachloroplatinum(IV) | 16.07 (15.96) | 2.87 (3.10) | 6.23 (6.20) |
| 8. | 1,4-DACH-dichlorodihyroxoplatinum(IV) | 17.47 (17.40) | 3.74 (3.89) | 6.76 (6.76) |
| 9. | 1,4-DACH-1,1-cyclobutane-dicarboxylatodichloroplatinum(IV) | 27.42 (27.59) | 3.89 (3.86) | 5.28 (5.36) |
| 10. | 1,4-DACH-oxalatodichloroplatinum(IV) | 20.68 (20.52) | 3.25 (3.25) | 5.89 (5.98) |
| 11. | 1,4-DACH-dichlorodiacetatoplatinum(IV) | 27.93 (28.00) | 3.83 (4.67) | 4.96 (5.03) |

*Cis-1,4-diaminocyclohexane

TABLE 2

IR and $^{195}Pt$ NMR spectroscopic data for platinum complexes.

| Complex No. | IR, $cm^{-1}$ | | | NMR, ppm $^{195}Pt$ |
|---|---|---|---|---|
| | $\nu N-H$ | $\nu C=O$ | $\nu_s C-O$ | |
| 1. | 3220 3140 | 1650 | 1380 | −1860 |
| 2. | 3160 | — | — | −1680 −1701 |
| 3. | 3100 3120 | 1620 | 1390 | −1622 |
| 4. | 3260 3200 | 1720 | 1400 | −1863 |
| 5. | 3150 3040 | 1650 | 1450 | −1831 |
| 6. | 3120 | 1600 | 1380 | −1859 |
| 7. | 3240 | — | — | −252 |
| 8. | 3150 | — | — | 885 |
| 9. | 3250 | 1600 | 1350 | 603 |
| 10. | 3260 | 1680 | 1350 | 623 |

EXAMPLE 2

The 1,4-DACH complexes synthesized as described in Example 1 were tested for cytotoxicity in vitro against murine leukemia L1210 cells and human ovarian A2780 cells.

Cytotoxic Evaluations

Cytotoxicity was determined by a modified MTT assay [22]. Briefly, the compounds were dissolved in normal saline and sterilized through 0.22 μm disc filters. The drug concentration was adjusted to 10 times the final upper concentration of a dose range and confirmed by FAAS. Aliquots (20 μl) of this, and serially diluted drug solutions, and of complete media (80 μl) were pipetted in triplicate into 96-well microtiter plates immediately before addition of cells. Cells in exponential phase of growth were trypsinized for 3 min, where necessary to dislodge adherent 2780 cells, collected and counted by Coulter counter (Coulter Electronics, Hialeah, Fla.). After diluting the L1210/0 (2,000/ml) and A2780 (5,000/ml) cells to appropriate concentrations, 100 μl aliquots of these cell suspensions were added to each of the wells. Following 5 (L1210 line) or 7 (2780 line) days of incubation in a 37° C., 5 % $CO_2$ humidified incubator, when control cells were in a exponential phase of growth, 50 μl of an MTT solution (3 mg/ml) was added to each well. After a 3 hour incubation, the medium was removed and replaced by 50 μl of 100% DMSO to dissolve MTT formazan crystals. Plates were then agitated on a plate shaker for 5 min, and absorbances were measured at 570 nm with a multiwell scanning spectrophotometer (Dynatech MR600, Chantilly, Va.).

$IC_{50}$s for the complexes described in Example 1 were determined against murine leukemia 1210/0 and human ovarian A2780 cells. Results are shown in Table 3.

TABLE 3

Cytotoxicity of cis-1,4-dach-Platinum (II) and (IV) complexes against Murine Leukemia L1210/0 and Human Ovarian A2780 cells.

| Complex No. | $IC_{50}$ (μM) | |
|---|---|---|
| | L1210/0 | A2780 |
| 1 | 1.60 | 0.43 |
| 2 | 0.08 | 0.05 |
| 3 | 0.28 | 0.13 |
| 4 | 0.50 | 0.11 |
| 5 | 0.24 | 0.051 |
| 6 | 0.34 | 0.058 |
| 7 | 0.12 | 0.20 |

TABLE 3-continued

Cytotoxicity of cis-1,4-dach-Platinum (II) and (IV) complexes against Murine Leukemia L1210/0 and Human Ovarian A2780 cells.

| Complex No. | IC$_{50}$ (μM) | |
|---|---|---|
| | L1210/0 | A2780 |
| 8 | 0.88 | 0.14 |
| 9 | 5.90 | 0.17 |
| 10 | 0.20 | 0.051 |
| 11 | — | 0.045 |
| Tetraplatin | 0.11 | 0.20 |
| Cis-platin | 0.23 | 0.36 |

Cytotoxicity data were obtained using an MTT assay and continuous drug exposure for 5 days.

EXAMPLE 3

Figure 1:
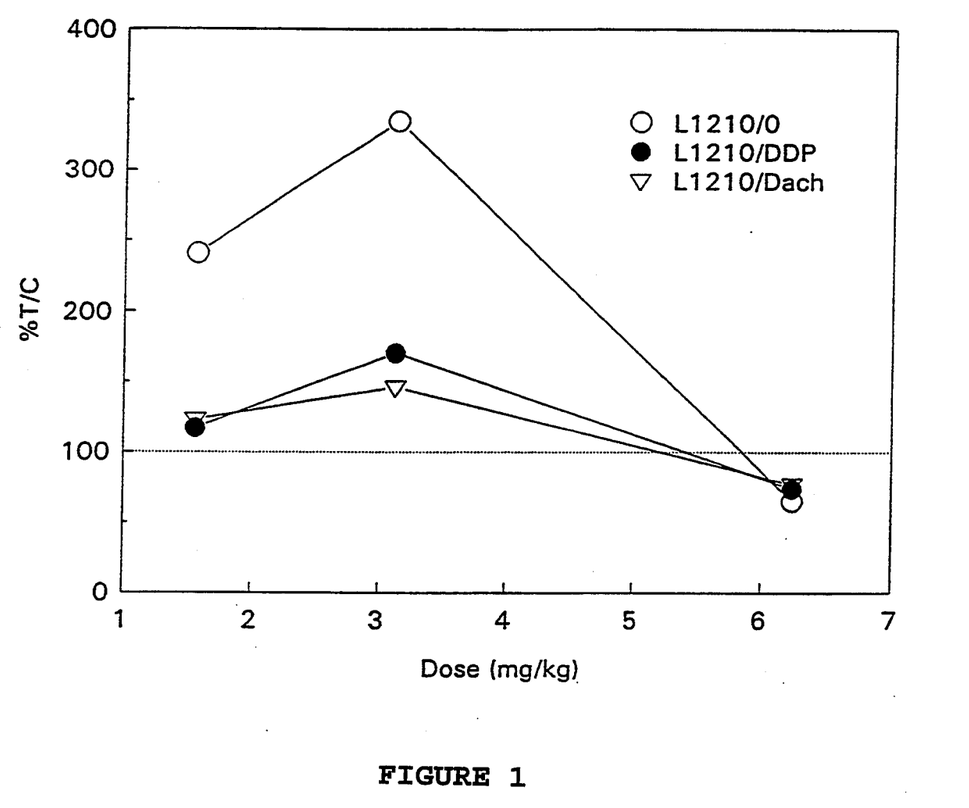
FIG. 1 shows the increased survival of mice treated with 1,4 DACH Pt(IV)-Cl$_4$ against L1210, DDP-resistant L1210 and DACH-resistant L1210.

Each of the platinum complexes was evaluated in vivo against L1210/0, L1210/DDP, L1210/DACH and M5076 cells at several dose levels. The dose-response relationship is exemplified in FIG. 1 using 1,4-DACH-Pt(IV)Cl$_4$ (compound 7) against L1210 lines. This complex had excellent activity against L1210/0 and good activities against L1210/DDP and L1210/DACH. The data at optimal doses are reproduced in Tables 5–7 along with data for the cyclobutanedicarboxylato, aquasulfato, methylmalonato and tartronato analogs (compounds 1–4 in Table 1).

Comparing data for 1,4-DACH-Pt(IV)Cl$_4$ (compound 7) with tetraplatin, it is observed that both complexes are active in L1210/0 and L1210/DDP models, with the 1,4-DACH-Pt complex having comparable or slightly greater activity (Table 5 and Table 7). These data were superior to those with cis-platin. Against L1210/DACH, which is resistant to tetraplatin and minimally sensitive to cis-platin, the 1,4-DACH-Pt(IV)Cl$_4$ complex had good activity (Table 6). Three other 1,4-DACH-Pt complexes were also highly active against the three cell lines. The 1,4-DACH-Pt(II)cyclobutanedicarboxylato complex (compound 1) was inactive against L1210/DDP cells (data not shown).

Figure 2:
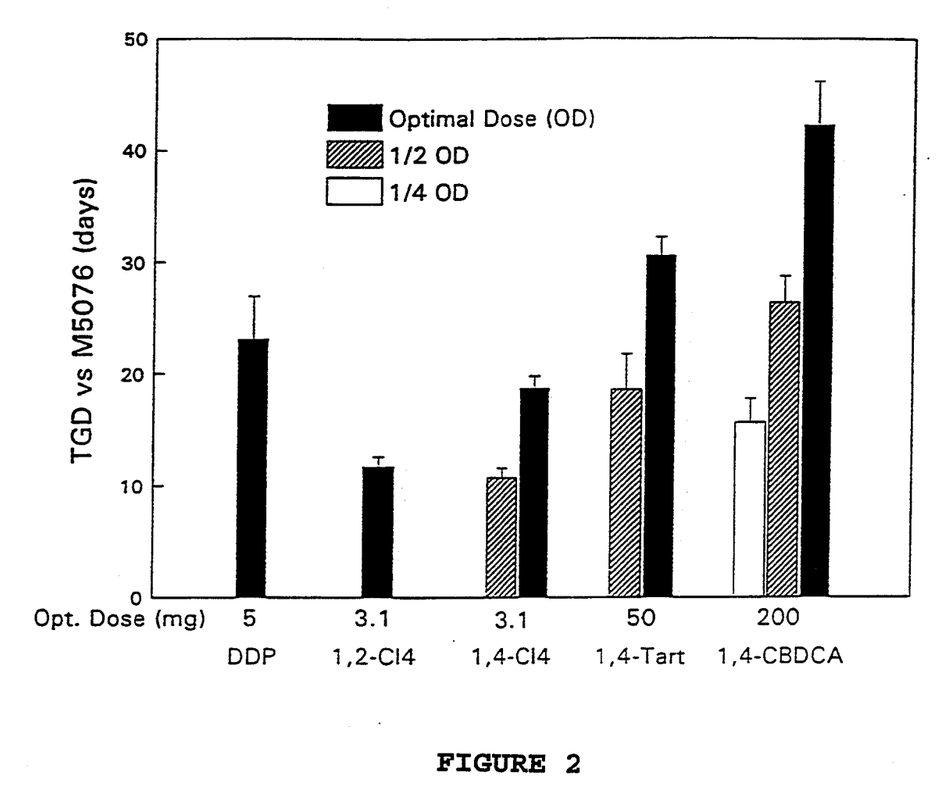
FIG. 2 shows the activity of the new platinum compounds against tumor M5076 at optimal dose levels, 50% of optimal dose levels and 25% of optimal dose levels. The compounds tested are shown as DDP=cis-platin; 1,2-Cl$_4$=tetraplatin; 1,4-Cl$_4$=1,4-DACH Pt(IV)-Cl$_4$; 1,4-Tart=1,4-DACH-Pt(II)tartronato; and 1,4-CBDCA=1,4-DACH-Pt(II) (1,1-cyclobutanedicarboxylato) complexes. TGD indicates tumor growth delay in days.

As indicated in Table 6, 1,4-DACH-Pt(II)tart (compound 4) was highly active against L1210/DACH cells, showing an 80% cure rate. The 1,4-DACH complexes also had excellent antitumor properties against M5076, against which tetraplatin was the least active (see FIG. 2 and Table 4). These results showed that the 1,4-DACH complexes had significantly greater selectivity than cis-platin and tetraplatin.

TABLE 4

Antitumor Data for 1,4-DACH-Pt(II) and Complexes Against M5076 Tumor Model

| Complex No. | MTD | TGD |
|---|---|---|
| 1 | 200 | 42.3 |
| 2 | 3.1 | 12.1 |
| 3 | 200 | 23.62 |
| 4 | 50 | 30.66 |
| 7 | 3.1 | 18.74 |
| Tetraplatin | 3.1 | 11.8 |

TABLE 4-continued

Antitumor Data for 1,4-DACH-Pt(II) and Complexes Against M5076 Tumor Model

| Complex No. | MTD | TGD |
|---|---|---|
| Cis-platin | 5.0 | 23.1 |

BDF1 mice inoculated s.c. with 10$^7$ M5076 cells on day 0 and drug administered i.p. on days 7, 14, 21, and 28. MTD = Maximum Tolerated Dose (mg/kg/injection), TGD = Tumor Growth Delay

TABLE 5

Antitumor Data For 1,4-DACH-Pt(II) and (IV) Complexes Against Murine Leukemia L1210/0.

| Complex No. | MTD | % T/C |
|---|---|---|
| 1 | 200 | 195 |
| 2 | 1.56 | >571 (3/5) |
| 3 | 200 | 382 (1/5) |
| 4 | 25 | 406 (1/5) |
| 7 | 3.1 | 335 (2/5) |
| Tetraplatin | 3.1 | 310 (2/5) |
| Cis-platin | 5.0 | 218 |

BDF1 mice inoculated i.p. with 10$^5$ L1210 Leukemia cells on day 0 and drug administered i.p. on days 1, 5, and 9. MTD = Maximum Tolerated Dose (mg/kg/injection), % T/C = (mean survival time of treated/mean survival time of control) × 100. Figures in parenthesis indicate long term survivors/no. tested.

TABLE 6

Antitumor Data For 1,4-DACH-Pt(II) and (IV) Complexes Against Murine Leukemia L1210/DACH.

| Complex No. | MTD | % T/C |
|---|---|---|
| 1 | 200 | 180 (1/5) |
| 2 | 1.56 | 140 (1/5) |
| 3 | 100 | 180 (1/5) |
| 4 | 50 | 343 (4/5) |
| 7 | 3.1 | 146 |
| Tetraplatin | 3.1 | 89 |
| Cis-platin | 5.0 | 127 |

BDF1 mice inoculated i.p. with 10$^5$ L1210 Leukemia cells on day 0 and drug administered i.p. on days 1, 5, and 9. MTD = Maximum Tolerated Dose (mg/kg/injection), % T/C = (mean survival time of treated/mean survival time of control) × 100. Figures in parenthesis indicate long term survivors/no. tested.

TABLE 7

Antitumor Data For 1,4-DACH-Pt (II) and (IV) Complexes Against Murine Leukemia L1210/DDP.

| Complex No. | MTD | % T/C |
|---|---|---|
| 4 | 50 | 187 |
| 7 | 3.1 | 170 (1/5) |
| Tetraplatin | 3.1 | 143 |
| Cis-platin | 5.0 | 100 |

BDF1 mice inoculated i.p. with 10$^5$ L1210 Leukemia cells on day 0 and drug administered i.p. on days 1, 5, and 9. MTD = Maximum Tolerated Dose (mg/kg/injection), % T/C = (mean survival time of treated/mean survival tune of control) × 100. Figures in parenthesis indicate long term survivors/no. tested.

Toxicity Studies

The complexes were administered as single ip doses that were estimated to be equitoxic from efficacy studies. As expected, cis-platin was nephrotoxic as indicated by high blood urea nitrogen (BUN) levels, and carboplatin and tetraplatin were myelosuppressive as shown by the observed leucopenia, Table 8. The 1,4-DACH complexes did not show any indication of nephrotoxicity or myelotoxicity with 1,4-DACH-Pt(II)CBDCA and 1,4-DACHPt(IV)Cl$_4$.

TABLE 8

Renal and Hematological Toxicities of 1,4-DACH-Pt(IV) Complexes

| Compound | Dose (mg/kg, i.p.) | Survivors on d. 14 | Body Wt. on d. 5 (% of control) | BUN d. 5 (mg %) | WBC d. 5 (× 10$^9$/l) |
|---|---|---|---|---|---|
| 1,4-DACH-Pt$^{II}$CBDCA | 300 | 5/5 | 99 | 18.0 | 5.25 |

TABLE 8-continued

| Renal and Hematological Toxicities of 1,4-DACH-Pt(IV) Complexes | | | | |
|---|---|---|---|---|
| Compound | Dose (mg/kg, i.p.) | Survivors on d. 14 | Body Wt. on d. 5 (% of control) | BUN d. 5 (mg %) | WBC d. 5 ($\times 10^9$/l) |
| 1,4-DACH-Pt$^{IV}$Cl$_4$ | 8.0 | 4/5 | 89 | 21.3 | 7.00 |
| Tetraplatin | 8.0 | 5/5 | 94 | 17.2 | 3.22 |
| Cis-platin | 12.0 | 5/5 | 81 | 35.3 | 5.58 |
| Carboplatin | 150 | 0/5 | 79 | 15.8 | 2.94 |
| Saline | — | 5/5 | 100 | 20.9 | 5.25 |

BDF1 mice were administered a single i.p. injection of the compound (5 mice/compound), and blood samples (50 μl) taken via the tail vein on day 5 for estimation of BUN and WBC as indices of renal and bone marrow toxicities respectively. The doses were estimated as equitoxic from the efficacy studies, where several doses of each compound were utilized. Results are presented as mean for clarity. S.D. were less than 20%.

While the compounds and methods of this invention have been described in terms of preferred embodiments, it will be apparent to those of skill in the art that variations may be applied to the compositions, methods and in the steps or in the sequences of steps of the methods described herein without departing from the concept, spirit and scope of the invention. More specifically, it will be apparent that certain agents which are both chemically and physiologically related may be substituted for the agents described herein while the same or similar results would be achieved. All such similar substitutions and modifications apparent to those skilled in the art are deemed to be within the spirit, scope and concept of the invention as defined by the appended claims. All claimed matter and methods can be made and executed without undue experimentation.

REFERENCES

The following references to the extent that they provide exemplary procedural or other details supplementary to those set forth herein are specifically incorporated herein by reference.

Abrams, M. J., Giandomenico, C. M., Murrer, B. A., and Vollano, J. F., U.S. Pat. No. 5,244,919, Sep. 14, 1993

Eastman, A., Schulte, N., Sheibani, N. and Sorenson, C. M. in Platinum and Other Metal Coordination Compounds in Cancer Chemotherapy (Proceedings of the Fifth International Symposium on Platinum and Other Metal Coordination Compounds in Cancer Chemotherapy, Padua, Italy, Jun. 29–Jul. 2, 1987), M. Nicolini, Ed., Martinus Nijhoff Publishing, Boston, 1987, pp. 178–195.

Khokhar, A. R., U.S. Pat. No. 5,041,578, Aug. 20, 1991.

Khokhar, A. R., Newman, R. A. and Krakoff, I. H., U.S. Pat. No. 5,011,959, Apr. 30, 1991.

What is claimed is:

1. A cis-1,4-diaminocyclohexane platinum (II) complex having the formula:

or a stereoisomer thereof, wherein Y is cyclobutanedicarboxylato, sulfato, methylmalonato, tartronato, oxalate, malonato or chloride.

2. A cis-1,4-diaminocyclohexane platinum (IV) complex having the formula:

or a stereoisomer thereof, wherein Y is chloride, cyclobutanedicarboxylato, methylmalonato, tartronato, oxalate or malonato and $X_1$ and $X_2$ are independently chlorine, hydroxyl, or acetate.

3. An antitumor composition which comprises a therapeutically effective amount of the platinum complex of claim 1 or claim 2 in a pharmaceutically acceptable vehicle.

4. A method of inhibiting neoplastic cell growth, comprising administering to a mammal an amount of the complex of claim 1 or claim 2 in an amount effective to inhibit neoplastic cell growth in said mammal.

5. The method of claim 4 wherein the neoplastic cell growth is tumor M5076.

6. The method of claim 4 wherein the neoplastic cell growth is leukemia L1210.

7. The method of claim 4 wherein the neoplastic cell growth is DDP resistant leukemia L1210.

8. The method of claim 4 wherein the neoplastic cell growth is human ovarian cells.

9. The method of claim 8 wherein the human ovarian cells are A2780 cells.

10. The method of claim 4 wherein the administration is by intraperitoneal administration.

11. The method of claim 4 wherein the neoplastic cell growth is DDP DACH resistant leukemia L1210.

* * * * *

UNITED STATES PATENT AND TRADEMARK OFFICE
CERTIFICATE OF CORRECTION

PATENT NO. : 5,393,909
DATED : February 28, 1995
INVENTOR(S) : Abdul R. Khokhar and Zahid H. Siddik It is certified that error appears in the above-indentified patent and that said Letters Patent is hereby corrected as shown below:

Title page, item [75], line 4, delete "Abdi" and insert --Abdul-- therefor.

In claim 1, column 12, line 18, after "Pt", insert --(II)-- therefor.

In claim 2, column 12, line 31, after "Pt", insert --(IV)-- therefor.

Signed and Sealed this

Twenty-fifth Day of April, 1995

Attest:

BRUCE LEHMAN

*Attesting Officer*     *Commissioner of Patents and Trademarks*